United States Patent [19]
Wade

[11] Patent Number: 5,693,931
[45] Date of Patent: Dec. 2, 1997

[54] SELF-CALIBRATING LABEL GAP SENSOR CIRCUIT WITH A CURRENT REGULATOR

[75] Inventor: Joseph R. Wade, Monroe, Wash.

[73] Assignee: Intermec Corporation, Everett, Wash.

[21] Appl. No.: 700,158

[22] Filed: Aug. 20, 1996

[51] Int. Cl.$^6$ ........................ G01J 1/32
[52] U.S. Cl. ................ 250/205; 250/559.1; 372/29
[58] Field of Search ................ 250/205, 206, 250/214 C, 214 RC, 559.1; 372/29–33

[56] References Cited

U.S. PATENT DOCUMENTS

| | | |
|---|---|---|
| 4,699,531 | 10/1987 | Ulinski, Sr. et al. . |
| 5,061,946 | 10/1991 | Helmbold et al. . |
| 5,061,947 | 10/1991 | Morrison et al. . |
| 5,248,879 | 9/1993 | Turvy, Jr. .................... 250/205 |
| 5,322,380 | 6/1994 | Crocker . |
| 5,335,837 | 8/1994 | Saeki et al. . |
| 5,480,244 | 1/1996 | Senda . |
| 5,492,423 | 2/1996 | Smith . |
| 5,498,087 | 3/1996 | Wey et al. . |
| 5,502,298 | 3/1996 | Geller ............................ 250/205 |

FOREIGN PATENT DOCUMENTS

| | | |
|---|---|---|
| 55-32603 | 3/1980 | Japan . |
| 60-187570 | 9/1985 | Japan . |
| 2-305666 | 12/1990 | Japan . |

*Primary Examiner*—Que Le
*Attorney, Agent, or Firm*—Graham & James LLP

[57] ABSTRACT

A label gap detection circuit comprises a photosensor having a light emitting element disposed at a first side of the print media and a light receiving element disposed at a second side of the print media so that light emitted by the light emitting element passes through the print media. The light emitting element provides a signal corresponding to an amount of light emitted therefrom and the light receiving element provides a signal corresponding to an amount of light received thereon. A regulator is coupled to the light emitting element for controlling an amount of light emitted by the light emitting element in response to a sum of the signals from the light emitting element and the light receiving element. An analog-to-digital converter is coupled to the light receiving element to receive the signal therefrom and provide a binary value corresponding to an amount of light received by the light receiving element. The label gap detection circuit is self-calibrating by use of current feedback from the light emitting and receiving elements of the photosensor to eliminate the need for potentiometers to calibrate the photosensor current level.

15 Claims, 2 Drawing Sheets

SELF-CALIBRATING LABEL GAP SENSOR CIRCUIT WITH A CURRENT REGULATOR

BACKGROUND OF THE INVENTION

1. Field of the Invention

The present invention relates to thermal transfer printing, and more particularly, to an apparatus for identifying the gap between adjacent labels of a thermal transfer print media which is capable of automatically and dynamically self-calibrating for media having widely differing light transmissive qualities.

2. Description of Related Art

In the field of bar code symbology, vertical bars of varying thicknesses and spacing are used to convey information, such as an identification of the object to which the bar code is affixed. The bar codes are typically printed onto paper substrate labels having an adhesive backing layer that enables the labels to be affixed to objects to be identified. To read the bar code, the bar and space elements are often scanned by a light source, such as a laser. Since the bar and space elements have differing light reflective characteristics, the information contained in the bar code can be read by interpreting the laser light that reflects from the bar code. Alternatively, the bar code may be imaged by a photosensitive element, such as a charge coupled device (CCD), and the individual bar and space elements identified from within a one or two-dimensional image of the bar code. In order to accurately read the bar code, it is thus essential that the bar code be printed in a high quality manner, without any streaking or blurring of the bar code. At the same time, it is essential that the adhesive backing layer of the labels not be damaged by heat generated during the printing process.

In view of these demanding printing requirements, bar codes are often printed using thermal transfer printing techniques. In thermal transfer printing, a print media is drawn between a platen and a thermal print head by a media transporting mechanism. A thermally active ink ribbon is transported in parallel with the print media between the platen and the thermal print head. The transporting mechanism may include stepper motors that transport the print media and the ink ribbon in small incremental steps of as little as two-hundred mils per step. The thermal print head has linearly disposed printing elements that extend across a width dimension of the print media. The printing elements are individually activated in accordance with instructions from a controller. As each printing element is activated, the thermally active chemical of the ribbon activates at the location of the particular printing element to transfer ink to the print media. The print media is continuously drawn through the region between the platen and the thermal print head, and in so doing, the bar code symbols are printed onto the print media as it passes through the region. Other images, such as text or symbols, can also be printed onto the print media in the same manner.

The print media may comprise a liner material onto which successive labels are affixed. The labels may be comprised of a paper substrate material having an adhesive backing that permit the labels to be applied to an object. The liner has a coating that permits the labels to be easily removed therefrom without adhering permanently, and which enables the labels to be effectively transported through the print region. There is usually a small gap between adjacent ones of the labels which is used to separate the labels and to provide for registration of the printed information to the labels, as further described below.

It is desirable within the art to maximize the amount of information printed on each label, and similarly, to reduce the amount of unused space on the labels. It is also desirable to avoid undesired mis-registration of printed information to a respective label. To accomplish these goals, it is necessary to identify with a high degree of accuracy the leading edge of each label on the print media in order to synchronize the printing with the transport of the print media. The gap between the adjacent labels is ideally a constant width, however, in practice, there are inevitable variations in the gap width caused by differences in print media production quality as well as due to stretching of the print media during its transport. For the printed information to begin as close as possible to the edge, it is necessary that the leading edge of the labels be identified within a single step size of the print media transporting mechanism.

To remedy this problem, gap sensor circuits are provided in the printers to identify the gap between adjacent labels of the print media. A conventional gap sensor circuit comprises a photosensor having a light emitting element and a light receiving element. The photosensor is disposed relative to the print media with the light emitting and receiving elements positioned at opposite sides of the print media thereof so that light passes through the print media as the media is transported. Since the regions of the media at which the label and liner are combined will transmit less light than the gap regions having the liner alone, the gap can be detected by the change in light transmissivity of the print media as it passes between the two photosensor elements.

A significant drawback of the conventional gap sensor circuits is that the photosensors must be periodically calibrated. Since there are inherent performance differences between individual photosensors, the gap circuits are provided with potentiometers that permit the current drawn by the photosensors to be adjusted during manufacture to calibrate the light emitting element to a standard light output value. The potentiometers further permit the photosensors to be recalibrated for use with different types of print media. As known in the art, print media may have widely differing light transmissive characteristics due to the particular material composition, thickness, or color of the labels and/or liner. In order to accurately detect the gap, there should be a discernable differential in light transmissivity between the combined liner/label and the liner alone. With a print media having a relatively opaque liner, for example, the light transmissivity differential may be too slight to detect a gap with sufficient accuracy. In such conditions, an operator of the printer may need to readjust the potentiometers in order to increase the light output. Subsequent use of the printer with a print media having a relatively transparent liner and/or label may require a readjustment to decrease the light output.

Thus, it would be desirable to provide an apparatus for detecting the gap between adjacent labels of a print media that does not require recalibration to increase or decrease the light output of the photosensor. Such an apparatus should automatically and dynamically calibrate itself for the changing operating conditions of the printer and for all types of print media.

SUMMARY OF THE INVENTION

In accordance with the teachings of the present invention, an apparatus for detecting a gap between adjacent labels of a print media is provided. The gap detection apparatus comprises an electrical circuit that is self-calibrating by use of current feedback from the light emitting and receiving elements of the photosensor, eliminating the need for potentiometers to calibrate the photosensor current level.

The gap detection circuit of the present invention comprises a photosensor having a light emitting element disposed at a first side of the print media and a light receiving element disposed at a second side of the print media so that light emitted by the light emitting element passes through the print media. The light emitting element provides a signal corresponding to an amount of light emitted therefrom and the light receiving element provides a signal corresponding to an amount of light received thereon. A regulator is coupled to the light emitting element for controlling an amount of light emitted by the light emitting element in response to a sum of the signals from the light emitting element and the light receiving element. An analog-to-digital converter is coupled to the light receiving element to receive the signal therefrom and provide a binary value corresponding to an amount of light received by the light receiving element.

More particularly, the regulator further comprises an operational amplifier having a non-inverting input coupled to a reference and an inverting input coupled to the light emitting element and the light receiving element to receive the sum of the signals therefrom. The operational amplifier has an output used to control a transistor that determines the amount of current drawn through the light emitting element. The transistor has a gate terminal coupled to the output of the operational amplifier, a collector terminal coupled to the light emitting element, and an emitter terminal coupled to the inverting input of the operational amplifier.

A more complete understanding of the self-calibrating label gap sensor circuit will be afforded to those skilled in the art, as well as a realization of additional advantages and objects thereof, by a consideration of the following detailed description of the preferred embodiment. Reference will be made to the appended sheets of drawings which will first be described briefly.

DETAILED DESCRIPTION OF THE PREFERRED EMBODIMENT

Figure 1:
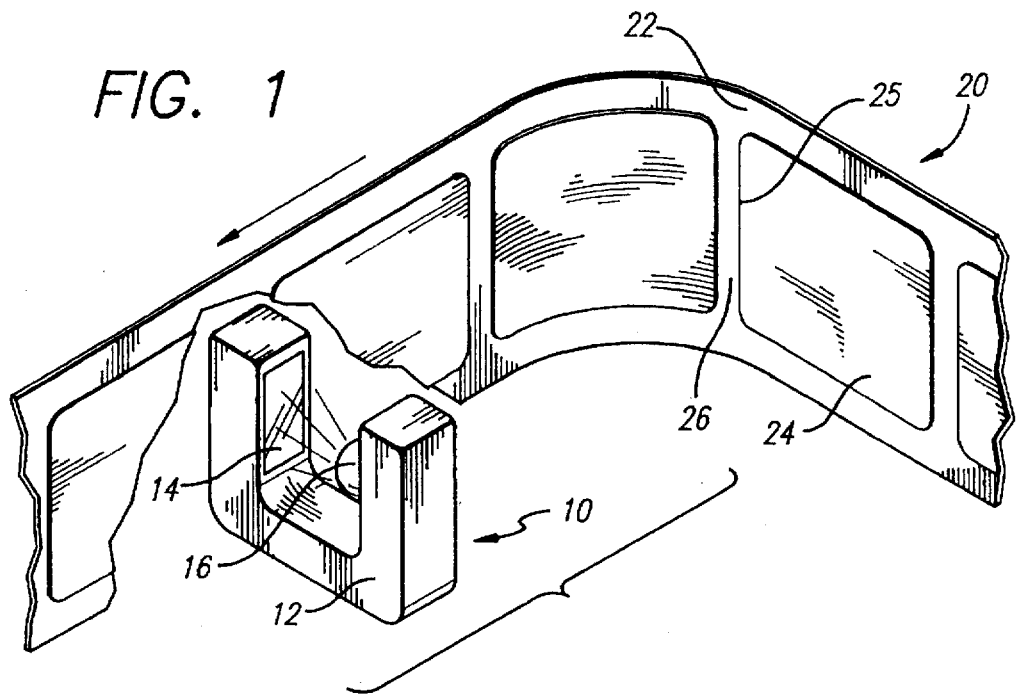
FIG. 1 is an illustration of a gap sensor used to monitor spacing of a print media.

The present invention satisfies the need for an apparatus for detecting the gap between adjacent labels of a print media that does not require recalibration to increase or decrease the light output of the photosensor. The label gap circuit of the present invention automatically and dynamically calibrates itself for the changing operating conditions of the printer and for all types of print media. In the detailed description that follows, it should be appreciated that like reference numerals are used to describe like elements illustrated in one or more of the figures.

Referring first to FIG. 1, a gap sensor 10 used to monitor spacing of a print media 20 is illustrated. The gap sensor 10 includes a U-shaped housing 12 that defines a slotted region through which the print media 20 is transported. A first surface of the housing 12 includes a light emitting element 16, and a second surface of the housing includes a light receiving element 14. The light emitting element 16 and light receiving element 14 are disposed so that they face each other across the slotted region. The light emitting element 16 may be provided by a conventional light emitting diode (LED) or photodiode, and the light receiving element 14 may be provided by a conventional phototransistor. Alternatively, the two elements of the gap sensor 10 may be provided in separate structural housings disposed in proximity to each other in the same manner as the single housing described above.

The print media 20 comprises a liner 22 having a glossy or inert surface onto which a plurality of labels 24 are affixed. The labels 24 comprise a paper substrate material having an exposed surface onto which information is printed and an adhesive surface opposite the exposed surface. The adhesive surface permits the labels 24 to remain affixed to the liner 22 as they are transported through the printer in a conventional manner. The labels 24 can be easily removed from the liner 22 after printing, enabling the labels to be permanently affixed to other objects for known identification purposes.

Gaps 26 are provided between adjacent ones of the labels 24, with the liner 22 exposed at the gaps. The width of each gap 26, or the spacing between adjacent ones of the labels 24, is generally a constant distance. The purpose of the gap sensor 10 is to accurately differentiate between the labels 24 the gap 26 so that printing can begin as close as possible to the leading edge 25 of a label. The liner 22 and labels 24 of the print media 20 permit a certain amount of light to pass therethrough, though it should be apparent that the label regions of the print media at which the labels are affixed are generally more opaque, i.e., less light transmissive, than the gap regions. Accordingly, the gap sensor 10 can identify the gaps 26 by detecting the difference in light transmissivity of the print media 20 as it is transported by a transporting mechanism (not shown) of the printer.

Figure 2:
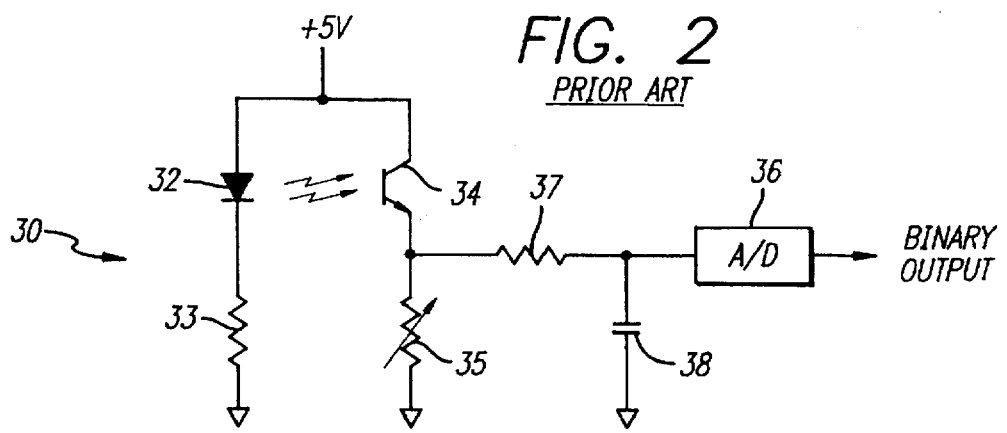
FIG. 2 is a schematic drawing of a conventional gap sensor circuit.

A conventional gap sensor circuit 30 is illustrated in FIG. 2. As known in the art, the light transmissivity of the respective gap and label regions will vary considerably between assorted types of print media due to differences in material composition, color and manufacturing standards. Therefore, the gap sensor circuit 30 permits the gain of the gap sensor to be increased in order to adjust for differences of light transmissivity.

More particularly, the conventional gap sensor circuit 30 includes a photodiode 32 and a phototransistor 34 that may be included in a common package, as described above. An anode terminal of the photodiode 32 and a collector terminal of the phototransistor 34 are commonly coupled to a voltage source which provides a direct current (DC) voltage, such as five volts (+5V). A cathode terminal of the photodiode 32 is coupled to ground through a resistor 33, and an emitter terminal of the phototransistor 34 is coupled to ground through a variable resistor or potentiometer 35. The emitter terminal of the phototransistor 34 is further coupled to an A/D converter 36 through a resistor 37, with a capacitor 38 coupling between the A/D converter and ground.

In operation of the gap sensor circuit 30, the five volt potential applied to the photodiode 32 causes a fixed current level determined by the value of the resistor 33 to be conducted through the photodiode, further causing the photodiode to emit a quantity of light determined by the fixed current level. The emitted light passes through the print media 20 as described above, with a first portion of the light being absorbed by the print media and a second portion of the light impinging upon the phototransistor 34. The phototransistor 34 becomes conductive in an amount proportional to the magnitude of light impinging thereon, causing current to flow between the collector and emitter terminals of the phototransistor to ground through the potentiometer 35.

A portion of the current from the emitter terminal of the phototransistor 34 conducts through the resistor 37 to the A/D converter 36, which generates a binary output value representing the instantaneous phototransistor current value for a given sample period. The capacitor 38 acts as a filter to smooth voltage transients at the A/D converter 36 that may be prevalent at start-up of the circuit 30 during which time the DC voltage is initially applied to the phototransistor 34. It should be apparent that the binary output of the A/D converter will vary directly with the amount of light transmitted between the photodiode 32 and the phototransistor 34, and can be used to detect the gap 26 between adjacent labels 24 of a print media 20, as described above.

The potentiometer 35 permits the amount of current conducted through the phototransistor 34 to be adjusted in order to calibrate the photosensor. Particularly, the potentiometer 35 can be adjusted to calibrate the phototransistor to conduct a predefined current level for the fixed light output from the photodiode 32. The potentiometer 35 can also be adjusted periodically to compensate for differences of light transmissivity of a particular print media 20 that is desired to be used on the printer. For example, a relatively opaque print media may not allow much light to penetrate therethrough causing the phototransistor 34 to conduct a relatively low amount of current at either of label or gap regions of the print media. Conversely, a relatively transparent print media may allow too much light to penetrate therethrough causing the phototransistor 34 to conduct a high amount of current at either of the label or gap regions of the print media. In both cases, the difference in current levels between the label region and gap region may not be significant enough to satisfactorily detect the gaps. Accordingly, the potentiometer 35 could then be adjusted to increase or decrease the current drawn through the phototransistor 34 to reach an acceptable operating range for the sensor circuit 30. As described previously, the adjustment of the potentiometer 35 is a somewhat cumbersome task that is prone to error, and is effectively avoided in the present invention.

Figure 3:
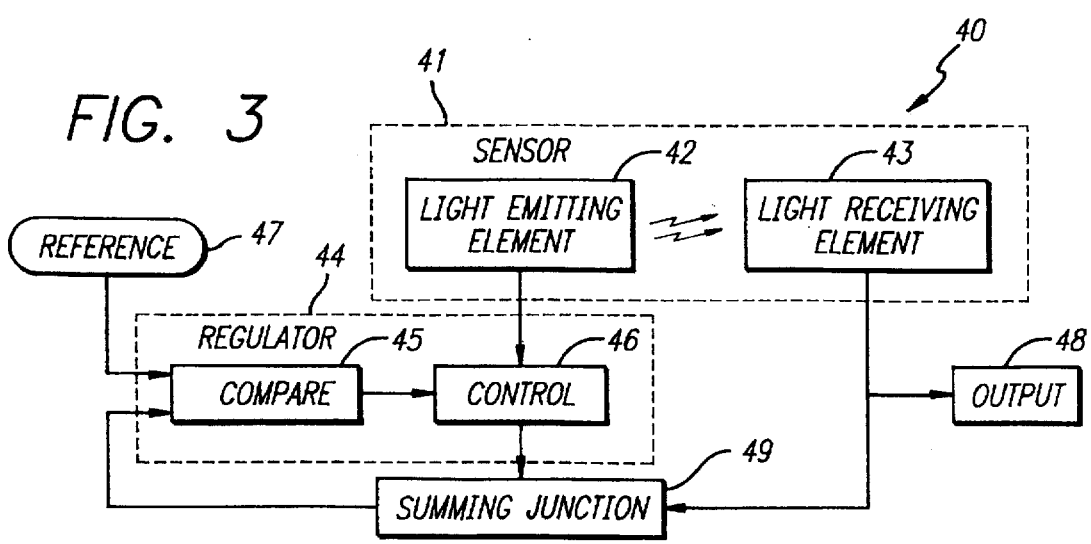
FIG. 3 is a block diagram of a gap sensor circuit of the present invention.

Referring now to FIG. 3, a block diagram of a gap sensor circuit 40 of the present invention is illustrated. As in the conventional gap sensor circuit 30 described above, a sensor 41 includes a light emitting element 42 and a light receiving element 43. The light receiving element 43 provides an output 48 that represents the instantaneous current value for a given sample period of the sensor 41. Unlike the conventional gap sensor circuit 30, the gap sensor circuit 40 of the present invention includes a current regulator 44 that controls the amount of current drawn by the light emitting element 42. A summing junction 49 combines the current from the light emitting and receiving elements 42, 43, and provides a combined current value to the current regulator 44. The current regulator 44 has a first element 45 that compares the combined sum of the current from the light emitting and receiving elements to a predetermined value provided by a reference 43, and a second element 46 that controls the current drawn by the light emitting element 42 based on the comparison.

The regulator 44 varies the amount of current drawn by the light emitting element 42, either by increasing or decreasing the current, in response to variations of the current drawn by the light receiving element 43. The light emitted by the light emitting element 42 will be increased in response to reductions in current at the light receiving element 43, such as due to a relatively opaque print media, and conversely, the light emitted by the light emitting element 42 will be decreased in response to increases in current at the light receiving element 43, such as due to a relatively transparent print media. The self-regulating operation of the gap sensor circuit 40 thus eliminates the need for potentiometers to calibrate the sensor current.

Figure 4:
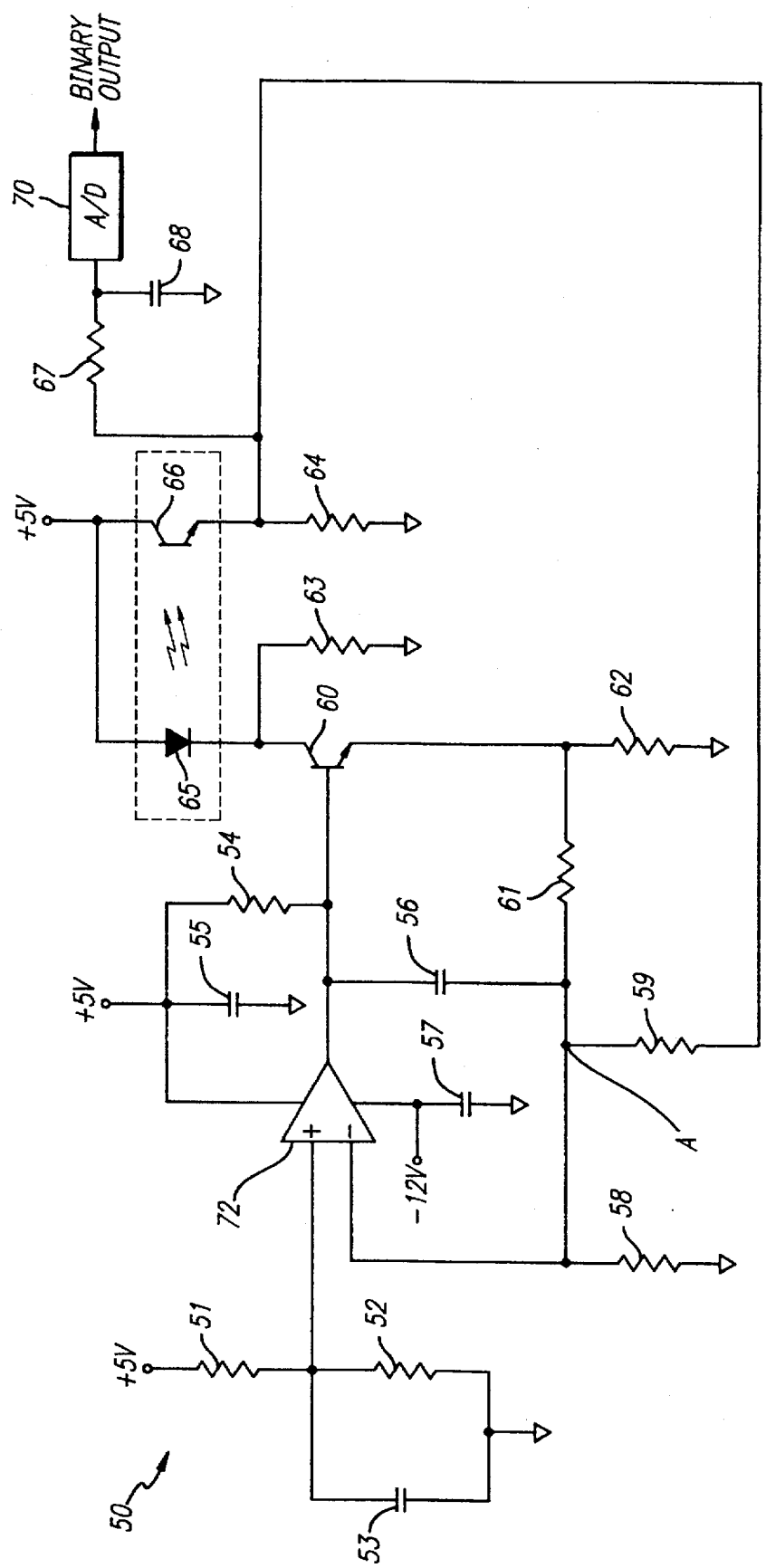
FIG. 4 is a schematic drawing an embodiment of the gap sensor circuit of FIG. 3.

A preferred embodiment of the gap sensor circuit of FIG. 3 is illustrated in schematic form in FIG. 4 as gap sensor circuit 50. Like the conventional gap sensor circuit 30 described above, the gap sensor circuit 50 includes a sensor having a photodiode 65 and a phototransistor 66. An anode terminal of the photodiode 65 and a collector terminal of the phototransistor 66 are commonly coupled to a voltage source which provides a direct current (DC) voltage, such as five volts (+5V). A cathode terminal of the photodiode 32 is coupled to ground through a resistor 63, and an emitter terminal of the phototransistor 66 is coupled to ground through a resistor 64. The emitter terminal of the phototransistor 66 is further coupled to an A/D converter 70 through a resistor 67, with a capacitor 68 coupling between the A/D converter and ground. Current from the emitter terminal of the phototransistor 66 conducts through the resistor 67 to the A/D converter 70, which generates a binary output value representing the instantaneous phototransistor current value for a given sample period. The capacitor 68 acts as a filter to smooth voltage transients at the A/D converter 70, as described previously.

The gap sensor circuit 50 further includes an operational amplifier 72 that provides the compare function of the regulator 44 of FIG. 3, and a transistor 60 that provides the current control function of the regulator. The operational amplifier 72 has a non-inverting input (+) coupled to a voltage divider circuit which provides a reference voltage level and an inverting input (−) that receives a current feedback signal from both the photodiode 65 and the phototransistor 66, as further described below. As known in the art, the operational amplifier 72 also includes two power terminals for applying DC input voltages, such as negative twelve volts (−12V) and five volts (+5V), with respective filter capacitors 57, 55 coupling the power terminals to ground. An offset resistor 54 provides a DC offset at the output terminal of the operational amplifier 72 so that there is at least a median positive voltage at the output terminal, with the output of the operational amplifier fluctuating above and below the median voltage depending on the voltage differential between the inverting and non-inverting inputs.

The voltage divider circuit includes a first resistor 51 coupled to a DC voltage source, such as five volts (+5V), and a second resistor 52 coupled in series with the first resistor and to ground. The non-inverting input of the operational amplifier 72 is coupled to the junction between the first and second resistors 51, 52. A capacitor 53 is coupled in parallel with the second resistor 52 to smooth voltage transients at the non-inverting input of the operational amplifier 72. As known in the art, the reference voltage can be determined by selecting the resistance values of the voltage divider circuit. In a preferred embodiment of the present invention, a reference voltage of 0.1 volts is achieved by use of a 50,000 ohm (50 KΩ) resistance value for the first resistor 51, and a 1,000 ohm (1 KΩ) resistance value for the second resistor 52.

The transistor 60 has a base terminal coupled to the output terminal of the operational amplifier 72, and a collector terminal coupled to the cathode terminal of the photodiode 65. An emitter terminal of the transistor 60 is coupled to a junction point A through a resistor 61, and is also coupled to ground through a resistor 62. The emitter terminal of the phototransistor 66 is also coupled to the junction point A through a resistor 59. The resistance values of the resistors 61 and 59 are selected to be equivalent, so that the current from each of the phototransistor 65 and the phototransistor 66 are approximately equal. In a preferred embodiment of the invention, a 100,000 ohm (100 KΩ) resistance value is selected for each of the resistors 61, 59. The junction point A is coupled to the inverting input of the operational amplifier 72, and is also coupled to ground through a resistor 58 so that the combined current at the junction point A produces an input voltage across the resistor 58 at the inverting input. It should be apparent that the current from each of the photodiode 65 and the phototransistor 66 is combined at the junction point A.

The operational amplifier 72 and the transistor 60 operate together to maintain the voltage at the junction point A across the resistor 58 at the reference voltage. When there is no difference between the reference voltage and the voltage at the junction point A, the output from the operational amplifier 72 is at the voltage determined by the offset resistor 54. As the amount of light received at the phototransistor 66 changes, such as by a transition from a label region to a gap region of a print media 20, the current through the resistor 59 will change accordingly.

For example, a decrease in light at the phototransistor 66 results in a decrease in current through the resistor 59 and a reduction in the voltage level at the inverting input of the operational amplifier. This produces a differential voltage between the inverting and non-inverting inputs of the operational amplifier 72, and produces a corresponding increase in the output voltage of the operational amplifier. As a result, the transistor 60 will be driven to conduct more current between its collector and emitter terminals, and in so doing, draw more current through the photodiode 65. The photodiode 65 would then emit a greater amount of light which, in turn, would cause a greater amount of light to impinge on the phototransistor 66. Eventually, this increase in current through both the photodiode 65 and the phototransistor 66 would restore the voltage at the inverting input across the resistor 58 to the reference voltage, returning the circuit to equilibrium with the output of the operational amplifier at the median voltage level. The gap sensor circuit 50 would compensate similarly for an increase in light at the phototransistor 66 in an opposite manner. Thus, the current applied to the photodiode 65 is continuously adjusted to maintain equilibrium with the current through the phototransistor 66, resulting in a greater range of print media having varying light transmissive characteristics.

It should be apparent that the gap sensor circuit of the present invention could also be advantageously utilized with other types of print media besides the media described above. For example, one type of alternative print media utilizes a printed paper stock that lacks any adhesive backing for use as printed tags. This alternative print media may include perforated separation lines between adjacent labels, and would not include a liner. At each of the perforated separation lines, a notch or indentation may be provided that extends at least partially inward from an outermost edge of the print media. The gap sensor circuit described above can be configured to recognize this indentation in the same manner as the gaps, as the indentation will have a different light transmissive characteristic than the rest of the print media. Moreover, an operator of a printer can change between different types of print media without having to recalibrate the gap sensor circuit.

Having thus described a preferred embodiment of a self-calibrating label gap sensor circuit, it should be apparent to those skilled in the art that certain advantages of the within system have been achieved. It should also be appreciated that various modifications, adaptations, and alternative embodiments thereof may be made within the scope and spirit of the present invention. The invention is further defined by the following claims.

What is claimed is:

1. An apparatus for detecting a gap between adjacent labels of a print media, comprising:

a photosensor having a light emitting element disposed at a first side of said print media and a light receiving element disposed at a second side of said print media so that light emitted by said light emitting element passes through said print media, said light emitting element providing a signal corresponding to an amount of light emitted therefrom and said light receiving element providing a signal corresponding to an amount of light received thereon; and a regulator coupled to said light emitting element for controlling an amount of light emitted by said light emitting element in response to a sum of said signals from said light emitting element and said light receiving element.

2. The apparatus of claim 1, wherein said light emitting element further comprises a photodiode.

3. The apparatus of claim 1, wherein said light receiving element further comprises a phototransistor.

4. The apparatus of claim 1, wherein said regulator further comprises an operational amplifier having a non-inverting input coupled to a reference and an inverting input coupled to said light emitting element and said light receiving element to receive said sum of said signals therefrom, said operational amplifier having an output used to control said light emitting element.

5. The apparatus of claim 4, further comprising a transistor having a gate terminal coupled to said output of said operational amplifier, a collector terminal coupled to said light emitting element, and an emitter terminal coupled to said inverting input of said operational amplifier.

6. The apparatus of claim 1, further comprising an analog-to-digital converter coupled to said light receiving element to receive said signal therefrom and provide a binary value corresponding to an amount of light received by said light receiving element.

7. An apparatus for detecting differences of light transmissivity for a transported media, comprising:

a first sensor element disposed at a first side of said media, said first sensor element emitting light having an amplitude corresponding to a first signal applied thereto;

a second sensor element disposed at a second side of said media so that said light emitted by said first sensor element passes through said media and impinges on said second sensor element, said second sensor element providing a second signal corresponding to an amount of light impinged thereon; and means for dynamically controlling an amount of light emitted by said first sensor element in response to a sum of said first and second signals.

8. The apparatus of claim 7, wherein said first sensor element further comprises a photodiode.

9. The apparatus of claim 7, wherein said second sensor element further comprises a phototransistor.

10. The apparatus of claim 7, further comprising an analog-to-digital converter coupled to said second sensor element to receive said second signal therefrom and provide a corresponding binary value corresponding.

11. The apparatus of claim 7, wherein said controlling means further comprises an operational amplifier having a first input coupled to a reference and a second input coupled to said first and second sensor elements to receive said sum of said first and second signals, said operational amplifier having an output used to vary said first signal.

12. The apparatus of claim 11, wherein said controlling means further comprises a transistor having a gate terminal coupled to said output of said operational amplifier, a collector terminal coupled to said first sensor element, and an emitter terminal coupled to said second input of said operational amplifier.

13. The apparatus of claim 11, wherein said first input of said operational amplifier comprises a non-inverting input and said second input of said operational amplifier comprises an inverting input.

14. In an apparatus for detecting differences of light transmissivity of a media comprising a light emitting element disposed at a first side of said media and a light receiving element disposed at a second side of said media whereby light emitted by said light emitting element passes through said media and impinges on said light receiving element, a self-calibration method comprises the steps of:

providing a first signal having an amplitude corresponding to a quantity of light emitted from said light emitting element and a second signal corresponding to a quantity of light impinged upon said light receiving element;

combining said first and second signals to provide a sum;

comparing said sum to a reference value to provide a difference signal; and regulating said first signal in response to said difference signal.

15. The method of claim 14, further comprising the step of providing a binary value corresponding to said second signal.

* * * * *